United States Patent
Herrera et al.

(10) Patent No.: US 10,982,207 B2
(45) Date of Patent: Apr. 20, 2021

(54) METHOD OF ISOLATING NUCLEIC ACIDS FOR LONG SEQUENCING READS

(71) Applicant: Roche Sequencing Solutions, Inc., Pleasanton, CA (US)

(72) Inventors: Monica Herrera, Livermore, CA (US); Jenny A. Johnson, Castro Valley, CA (US); Yuan Qin, Dublin, CA (US); Kunchala Rungsrisuriyachai, Dublin, CA (US); Smriti Sharma, Fremont, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 72 days.

(21) Appl. No.: 16/276,555

(22) Filed: Feb. 14, 2019

(65) Prior Publication Data

US 2019/0177715 A1    Jun. 13, 2019

Related U.S. Application Data

(63) Continuation of application No. PCT/EP2017/069449, filed on Aug. 1, 2017.

(60) Provisional application No. 62/375,244, filed on Aug. 15, 2016.

(51) Int. Cl.
*C12N 15/10* (2006.01)
*C07H 1/08* (2006.01)

(52) U.S. Cl.
CPC ..... *C12N 15/1013* (2013.01); *C12N 15/1006* (2013.01); *C07H 1/08* (2013.01)

(58) Field of Classification Search
None
See application file for complete search history.

(56) References Cited

U.S. PATENT DOCUMENTS

| | | | |
|---|---|---|---|
| 8,008,475 B1 | 8/2011 | Bastian et al. | |
| 2005/0079535 A1 | 4/2005 | Kirchgesser et al. | |
| 2009/0088560 A1* | 4/2009 | Shen | C12N 15/1006 536/23.1 |
| 2014/0080784 A1* | 3/2014 | Stover | A61N 5/10 514/50 |
| 2014/0093888 A1* | 4/2014 | Templeton | G01N 33/573 435/7.4 |
| 2015/0159221 A1* | 6/2015 | Seeger | G16B 25/00 506/9 |

FOREIGN PATENT DOCUMENTS

| DE | 19746874 A1 | 4/1999 |
|---|---|---|
| EP | 1524317 A1 | 4/2005 |

OTHER PUBLICATIONS

Ahern, The Scientist 9 (15), 20 (1995).*
Hill, V. R. et al, Development of a Nucleic Acid Extraction Procedure for Simultaneous recovery of DNA and RNA from Diverse Microbes in Water, Pathogens, (2015), pp. 335-354, vol. 4, No. 2.
International Search Report and Written Opinion dated Oct. 17, 2017 in connection with PCT/EP2017/069449 filed Aug. 1, 2017 (33804 WO), pp. 1-16.
Qiagen, For highly efficient purification of viral RNA and DNA from 1 ml plasma and serum samples, QIAamp_UltraSens_Viurs Handbook, (2012), pp. 1-24, -, Qiagen.
Schlappi, T. S. et al, Flow-through Capture and in Situ Amplification Can Enable Rapid Detection of a Few Single Molecules of Nucleic Acids from Several Milliliters of Solution, Analytical Chemistry, (2016), pp: 7647-7653, vol. 88.

* cited by examiner

*Primary Examiner* — James Martinell
(74) *Attorney, Agent, or Firm* — Olga Kay

(57) ABSTRACT

The invention is a novel method of isolating long nucleic acids from samples suitable for nucleic acid sequencing. The method is especially suitable for isolating low-concentration nucleic acids, e.g., viral nucleic acids, from clinical samples.

13 Claims, 2 Drawing Sheets

METHOD OF ISOLATING NUCLEIC ACIDS FOR LONG SEQUENCING READS

CROSS-REFERENCE TO RELATED APPLICATIONS

This patent application is a continuation of International Patent Application No. PCT/EP2017/069449 filed Aug. 1, 2017, which claims priority to and the benefit of U.S. Provisional Application No. 62/375,244, filed Aug. 15, 2016. Each of the above patent applications is incorporated herein by reference as if set forth in its entirety.

FIELD OF THE INVENTION

The invention relates to the field of nucleic acid isolation. More specifically, the invention relates to the field of isolating long nucleic acid molecules that can be used, for example, in sequencing applications.

BACKGROUND OF THE INVENTION

Existing methods of isolating nucleic acids result in breakage or chemical degradation of a portion of the nucleic acid resulting in recovery of short strands (<500 bp). The problem is especially severe for single-stranded nucleic acids, including RNA. At the same time, contemporary detection technologies, such as real-time quantitative PCR, are able to detect nucleic acids at very high sensitivity, i.e., when a very low copy number of the target nucleic acid (e.g., viral RNA) is present in the sample since they often target short nucleotide strands. However, since the advent of long-read next generation sequencing (NGS), the requirements for nucleic acid isolation have changed and require a more sensitive method to take advantage of long-read NGS as a cutting edge diagnostic tool, e.g., for detecting viral targets. In order to accomplish this, there is a necessity to recover and amplify nucleic acid molecules greater than 1,000 bp in length. Certain single-stranded nucleic acids, including viral RNA molecules are inherently more delicate and easily degraded as compared to DNA molecules during traditional nucleic acid extraction protocols.

SUMMARY OF THE INVENTION

Provided herein are novel methods for isolating nucleic acids from a sample for long read sequencing.

In some embodiments, the method comprises providing a liquid sample; contacting the sample with a lysis buffer comprising a reducing agent, a detergent, a carrier molecule and a protease; contacting the sample to a nucleic acid-retaining separation matrix to bind the nucleic acid; contacting the matrix with the bound nucleic acid with a wash solution; eluting the nucleic acid with elution buffer to obtain elution volume; and concentrating the elution volume at least 2-fold. In some embodiments, the method comprises a precipitation and a resuspension step prior to lysis or prior to binding to the matrix. In some embodiments, binding to the matrix is in the presence of alcohol. In some embodiments, the nucleic acid is RNA and the matrix with the bound nucleic acid is treated with DNase. In some embodiments, the nucleic acid is DNA and the matrix with the bound nucleic acid is treated with RNase. In some embodiments, the sample is a patient's sample. In some embodiments, the sample is a liquid sample selected from cerebrospinal fluid, saliva, urine, a tissue extract or a cell culture supernatant; or liquid comprising cells derived from tissue, tissue fragments or cell culture. In some embodiments, prior to lysis, the sample is precipitated in the cold. In some embodiments, the lysis buffer is added in two steps: the first lysis buffer comprising a reducing agent, a detergent, and a carrier molecule; and the second lysis buffer comprises a protease and a chaotropic agent and has high ionic strength. In some embodiments, the nucleic acid-retaining separation matrix is selected from magnetic glass particles, silica particles or silica membrane. In some embodiments, the elution buffer comprises a preservative. In some embodiments, the concentrating is by passing the elution volume through a semipermeable polymer membrane. The polymer membrane can be cellulose acetate, nylon, polyether, polyether sulfone. The membrane can have a molecular weight cut-off of 100 kDa. In some embodiments, the concentrating is performed after combining several elution volumes. In some embodiments, the nucleic acid is eukaryotic DNA or RNA, prokaryotic DNA or RNA, or viral DNA or RNA. In some embodiments, after the protease digestion, the remaining steps are performed at lowered temperatures.

In some embodiments, a kit is provided for isolating nucleic acid from a sample comprising: a first lysis buffer comprising a reducing agent, a detergent, and a carrier molecule; a second lysis buffer, comprising a protease; a nucleic acid retaining matrix and a concentrating polymer. The kit may also comprise DNase or RNase.

In some embodiments, a method is provided for isolating viral nucleic acids comprising providing a liquid sample; obtaining a first precipitate from the sample; contacting the first precipitate with a first lysis buffer comprising a reducing agent, a detergent, and a carrier molecule; obtaining a second precipitate; contacting the second precipitate with a second lysis buffer comprising a protease under the conditions where protease is active; obtaining a third precipitate; contacting the third precipitate with a buffer comprising an alcohol; contacting the sample with a nucleic acid-retaining separation matrix to bind the nucleic acid; contacting the matrix with a wash solution; eluting the nucleic acid with elution buffer to obtain elution volume; concentrating the elution volume at least 2-fold.

DETAILED DESCRIPTION OF THE INVENTION

Fourth generation sequencing technologies promise detection of rare target nucleic acids with unprecedented sensitivity. For example, very low concentration of viral nucleic acids can be detected in blood and plasma samples from infected patients with very low viral load. The sensitivity of the sequencing technology however is limited by the ability to recover the target from the sample. Existing methods of isolating nucleic acids, e.g., isolating viral nucleic acids or circulating cell-free nucleic acids from blood or plasma samples fail to yield detectable amounts of target nucleic acids. Furthermore, current sequencing technologies are making strides in the ability to sequence longer targets. The advantage of longer reads is the ability to phase genotypes, including viral genotypes and human genotypes related to the protein structure. Current methods of isolating nucleic acids often yield fragmented nucleic acids thus negating the progress of the sequencing technologies.

Figure 1:
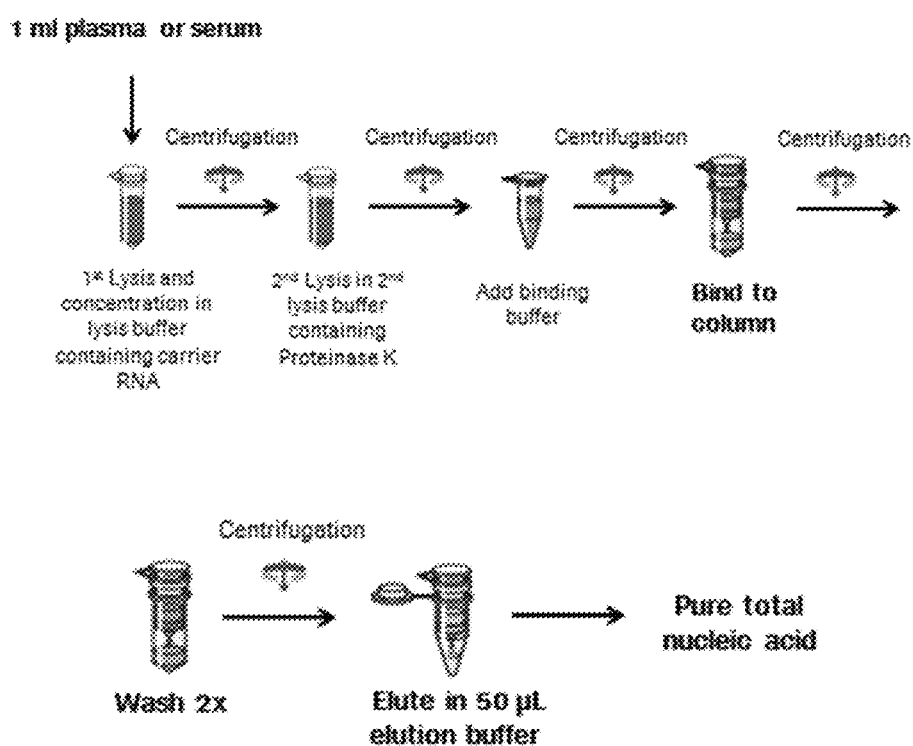
FIG. 1 is a diagram of a prior art method of isolating viral nucleic acids.
Figure 2:
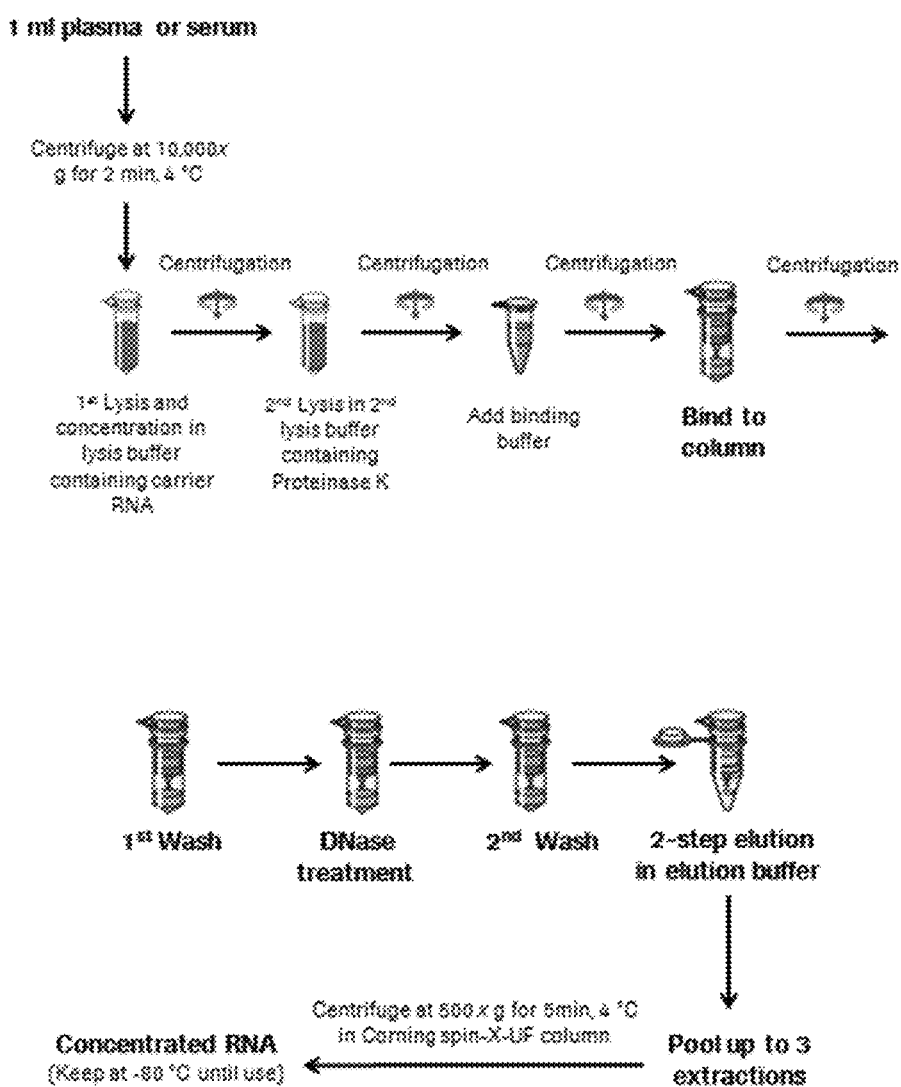
FIG. 2 is a diagram of a novel method of isolating intact long nucleic acid from a liquid sample.

Provided herein are new methods and kits that utilize existing tools and reagents for nucleic acid isolation to create a novel workflow with unexpected results. As is shown in FIG. 1, the current methods include optional cell lysis, digestion of proteins, wash and recovery of total nucleic acids using an affinity binding column. This method produced insufficient yields for existing sensitive detection methods, especially for longer templates, e.g. >300 bp, >500 bp, or >1000 bp.

The presently disclosed methods provide a gentler extraction protocol (e.g., at lower temperature, e.g., 22-55 C, <56 C, 37-42 C) to prevent degradation of nucleic acids, in particular RNA. In addition, there are two elution steps, also at lower temperature, to ensure complete removal of nucleic acids from the selected binding matrix. Where RNA is being isolated, the present methods also include a DNase treatment step.

In some embodiments, the invention is a method of isolating nucleic acid from a sample. The sample may be derived from a subject or a patient. In some embodiments, the sample comprises cells or tissue or tissue fragments. In some embodiments the sample may comprise a body fluid (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, and/or suspended in a fluid fecal samples). The sample may comprise whole blood or blood fractions. In some embodiments, the sample, especially the liquid sample may comprise cell-free material such as cell-free DNA or RNA including cell-free tumor DNA or tumor RNA. The sample may comprise an intact infectious agent (a *bacterium*, a protozoan, a virus or a *mycoplasma*) or nucleic acids (DNA or RNA) from the infectious agent. In other embodiments, the sample is an in vitro cultured sample, e.g., a cell culture or cell culture supernatant or containing or suspected to contain an infectious agent or nucleic acids derived from the infectious agent of from the cultured cells. In some embodiments, the infectious agent is a *bacterium*, a protozoan, a virus or a *mycoplasma*. In some embodiments, the cell is a eukaryotic (including human patient) cell. In some embodiments, the cell is a prokaryotic cell.

A target nucleic acid is the nucleic acid of interest that may be present in the sample and isolated when the nucleic acids from the sample are isolated. The target nucleic may be from a host genome or from an infectious agent infecting the host cell or the host organism. In some embodiments, the target nucleic acid is a mammalian (including human patient) nucleic acid. In some embodiments, the target nucleic acid is bacterial or viral nucleic acid or nucleic acid derived from other infectious organisms. In some embodiments, the target nucleic acid is a gene or a gene fragment. In other embodiments, the target nucleic acid contains a genetic variant, e.g., a polymorphism, including a single nucleotide polymorphism or variant (SNP of SNV), or a genetic rearrangement resulting e.g., in a gene fusion. In some embodiments, the target nucleic acid comprises a biomarker. In other embodiments, the target nucleic acid is characteristic of a particular infectious organism and aids in identification of the infectious organism or a characteristic of the infectious organism, e.g., drug sensitivity or drug resistance. In some embodiments, the target nucleic acid is between 100 bases or base pairs and 10,000 bases or base pairs long. In some embodiments, the target nucleic acid is >1,000 bases or base pairs long.

In some embodiments, the method comprises obtaining a precipitate. In some embodiments, the precipitate is obtained by centrifugation. In some embodiments, other methods of obtaining the dissolved materials are chemical precipitation and filtration. In some embodiments, centrifugation is performed at ambient temperature. In other embodiments, the centrifugation is performed at low temperature, e.g., 4° C. In some embodiments, the precipitate is obtained between every step of the method where one liquid is to be replaced with another liquid.

In some embodiments, the method comprises a lysis buffer for lysing cells and subcellular structures, e.g., viral particles and viral capsids. In some embodiments, the lysis buffer comprises one or more of a reducing agent, a detergent, a carrier molecule, high ionic strength salt (e.g., 25-250 mM or 50-100 mM Tris-HCl or NaCl), a chaotropic agent and a protease. In some embodiments, the lysis buffer is added at ambient temperature while in other embodiments, the lysis buffer is added at elevated temperature e.g., between 40° C. and 65° C. In some embodiments, the lysis buffer is added at <56° C., e.g., 40° C.-56° C., 37° C.-42° C. or 20° C.-55° C.

In some embodiments, the reducing agent is selected from DTT and 2-mercaptoethanol. The selected reducing agent is typically present at a concentration of 1-10 mM in final concentration. In some embodiments, the detergent is selected from an anionic detergent (e.g., SDS, LDS), cationic detergent, non-ionic detergent (Tween, Triton), and zwitterionic detergent (e.g., CHAPS). The selected detergent is typically present at a concentration of about 0.1-0.5% (w/v) in final solution. In some embodiments, the carrier molecule is carrier RNA, e.g., at a concentration of about 0.5 mg/ml in final solution. In some embodiments, the chaotropic agent is selected from guanidinium thiocyanate, guanidinium chloride, urea, and lithium perchlorate. The selected chaotropic agent is typically present at a concentration of 2-7 M, e.g., 3-5 M or 4 M in final solution. In some embodiments, the protease is proteinase K, but can be a serine, cysteine, threonine, aspartic, or glutamic protease. The selected protease is typically present at a concentration of 50-100 ug/ml in final solution.

In some embodiments, following the protease digestion, the remaining steps are performed at lowered temperatures, e.g., 4° C. to minimize degradation of nucleic acids.

In some embodiments, the solution containing target nucleic acids is contacted to a nucleic acid-retaining separation matrix to bind the nucleic acids. In some embodiments, the nucleic acid-retaining separation matrix is selected from magnetic glass particles, silica particles or silica membrane. In some embodiments, binding of the nucleic acids to the matrix is chemically facilitated, e.g., by adding alcohol to the solution of target nucleic acids or to the matrix.

In some embodiments, the matrix with bound nucleic acids is washed one or more times to effect removal of impurities. The wash buffer can include ethanol, guanidinium thiocyanate, and/or sodium azide. Washing can be carried out at room temperature, 18-42° C., or 30-37° C. In some embodiments, the nucleic acids are eluted from the nucleic acid retaining matrix with an elution buffer. The elution buffer can include a buffer, e.g., Tris at 5-20 mM or about 10 mM, at pH8-8.5. In some embodiments, the elution buffer comprises a preservative, e.g., sodium azide.

In some embodiments, the eluted nucleic acids are treated with a nuclease. In some embodiments, the target nucleic acid is RNA in which case the sample is treated with DNase.

In other embodiments, the target nucleic acid is DNA in which case the sample is treated with RNase.

In some embodiments, the solution of nucleic acids in the elution buffer is concentrated. In some embodiments the concentrating is by passing the elution volume through a semipermeable membrane retaining the nucleic acids. In some embodiments, the membrane is a polymer membrane selected from cellulose acetate, nylon, polyether, and polyether sulfone. The membrane may have a molecular weight cut-off, e.g., of 100 kDA. In some embodiments, the concentrating is performed after combining several elution volumes.

As is shown in Table 1 and Table 2, the novel method increases the sensitivity expressed as limit of detection (LOD) at least 10 fold.

TABLE 1

Prior art Limits of Detection (LOD)

| Sample type | LOD |
| --- | --- |
| HCV plasma specimens | 10,000 IU/mL |
| HIV plasma specimens | 1,000 copies/mL |
| Cultured HIV sample | 1,000 copies/mL |

TABLE 2

LOD of the novel method

| Sample type | New LOD |
| --- | --- |
| HCV plasma specimens | 1,000 IU/mL |
| HIV plasma specimens | 100 copies/mL |

In some embodiments, the isolated target nucleic acids are subjected to downstream analysis. The downstream analysis may include in vitro amplification (PCR or RT-PCR), capture by hybridization or nucleic acid sequencing. Recovery of the target nucleic acids can be measured as the ability to detect the target nucleic acids by these analysis methods. Yield can be expressed as the amount or concentration of nucleic acid recovered. Yield can also be expressed as the amount of product (e.g., amplicon) generated from the recovered nucleic acid. Sensitivity can be expressed as the limit of detection (LOD). Limit of detection (LOD) can be measured as the lowest amount of target to detectably recover target nucleic acid which is detected directly (e.g., concentration measurement) or indirectly (e.g., presence and/or amount of amplicons).

Surprisingly, the inventors observed that the method of the invention yields the most improvement in recovery of longer nucleic acid fragments, especially from samples with low nucleic acid concentration, e.g., low viral load (Table 3). Further surprising is the effect of concentration: a 3-fold concentration results in up to 5-fold and 8-fold improvement in yield (Tables 4 and 5). While the disclosed examples relate to viral load copy numbers, the presently disclosed methods can be used to isolate non-viral nucleic acid targets (e.g., transcripts, biomarkers, etc.).

In some embodiments, the invention is a kit for isolating nucleic acid from a sample. In the kit, some or all the reagents and solutions used in the method of the invention are packaged together with the instructions for performing the method described herein. The kit may comprise one or more lysis buffers comprising a reducing agent, a detergent, and a carrier molecule, a protease, a chaotropic agent and salt. The kit may further comprise a nucleic acid-retaining matrix and a concentrating polymer. The kit may further comprise nuclease such as DNase or RNase.

TABLE 3

Significant improvement in product yield for long amplicons (3.2 kb)

| Sample Viral Loads (copies/mL) | Default Protocol Amplicon yield (ng/ul) | New protocol Amplicon yield (ng/ul) | % Difference |
| --- | --- | --- | --- |
| 100,000 | 44.57 ± 40.63 | 117.82 ± 71.7 | 164% |
| 10,000 | 6.24 ± 7.85 | 57.26 ± 44.12 | 817% |
| 1,000 | 0.36 ± 0.1 | 13.66 ± 9.42 | 369% |
| 100 | 0.8 | 6.34 ± 8.56 | 692% |

EXAMPLES

Example 1. Isolating HIV-1 RNA from Human Plasma Samples

Clinical Specimens:

Plasma samples of six patients, including HIV Subtype A and B, were obtained. The samples were quantified for viral loads and genotyped using COBAS® Ampliprep/COBAS® TaqMan® (CAP/CTM) platform (Roche Diagnostics, GmbH, Mannheim, Germany). Samples with a viral load of about 100,000 copies/ml were selected. The samples were diluted in HIV negative plasma to the concentrations used in this study.

Viral RNA Isolation:

The viral RNA isolation in this study was performed using the QIAamp UltraSens Virus Kit from QIAgen (Valencia, Calif.). The default method was performed per the manufacturer's protocol with input volume of 1.0 ml plasma sample and final elution volume at 50 μL. For the in-house optimized protocol, approximately 1.2 ml of plasma samples was centrifuged at 10,000×g at 4° C. for 2 minutes. The isolation was performed per manufacturer's instructions with the following modifications. After the first wash step, 30 Units of DNase I was added into the QIAgen column and incubated at 25° C. for 15 minutes. The DNase I was removed by the second wash step. Elution was performed in two steps of centrifugation at different volume, 30 μL and 45 μL, to have final volume of 75 μL pure RNA. To concentrate RNA, up to 3 RNA extractions (~225 μL) were pooled and centrifuged at 500×g at 4° C. for 5 minutes with Corning spin X-UF column from (Corning, Lowell, Mass.) to obtain final volume approximate 50 μL.

The lysis buffer includes DTT, 2-mercaptoethanol, SDS, carrier RNA, or similar components. The wash buffer includes ethanol, guanidinium thiocyanate, sodium azide, or similar components. The QIAgen elution buffer includes Tris at about 10 mM, pH8-8.5. The QIAgen column is silica membrane.

The concentrated RNA was used to generate amplicons by RT-PCR of target size 2.2 kb and 3.2 kb comparing both the default and optimized isolation method. The amount of amplicons was measured directly on Fragment Analyzer™ instrument (Advanced Analytical Technologies, Inc. Ankeny, Iowa). Results are shown in Tables 4 and 5.

TABLE 4

Product yield for long amplicons (2.2 kb)

| Sample Viral Loads (copies/ml) | Default manufacturer's UltraSens Protocol Average amplicon yield (ng/ul) | Novel Method Average amplicon yield (ng/ul) | % Difference |
|---|---|---|---|
| 100,000 | 39.12 ± 44.43 (n = 8) | 125.6 ± 59.44 (n = 8) | 221% |
| 10,000 | 20.26 ± 9.55 (n = 12) | 68.79 ± 52.62 (n = 6) | 240% |
| 1,000 | 2.41 ± 0.16 (n = 2) | 14.48 +/− 4.89 (n = 4) | 501% |
| 100 | 2.17 ± 1.59 (n = 4) | 3.2 ± 3.92 (n = 2) | 48% |

TABLE 5

Product yield for long amplicons (3.2 kb)

| Sample Viral Loads (copies/ml) | Default UltraSens Protocol Average amplicon yield (ng/ul) | Novel Method Average amplicon yield (ng/ul) | % Difference |
|---|---|---|---|
| 100,000 | 44.57 ± 40.63 (n = 7) | 117.82 ± 71.7 (n = 16) | 164% |
| 10,000 | 6.24 ± 7.85 (n = 8) | 57.26 ± 44.12 (n = 16) | 817% |
| 1,000 | 0.36 ± 0.1 (n = 4) | 13.66 ± 9.42 (n = 11) | 369% |
| 100 | 0.8 (n = 1) | 6.34 ± 8.56 (n = 5) | 692% |

The invention claimed is:

1. A method of isolating nucleic acid from a sample comprising
    (a) providing a liquid sample;
    (b) contacting the sample with a first lysis buffer comprising a reducing agent, a detergent, and
    (c) contacting the sample with a second lysis buffer having high ionic strength and comprising a protease and a chaotropic agent;
    (d) contacting the sample to a nucleic acid-retaining separation matrix to bind the nucleic acid;
    (e) contacting the matrix with the bound nucleic acid with a wash solution;
    (f) eluting the nucleic acid with elution buffer to obtain elution volume;
    (g) pooling at least two elution volumes from the sample; and
    (h) concentrating the pooled elution volume from step (g) at least 2-fold by passing the pooled elution volume through a semipermeable polymer membrane.

2. The method of claim 1, wherein the method comprises a centrifuge step and a precipitate resuspension step prior to step (b) and prior to step (c).

3. The method of claim 2, wherein prior to lysis, the sample is precipitated at 4° C.

4. The method of claim 1, wherein binding to the matrix is in the presence of alcohol.

5. The method of claim 1, wherein the nucleic acid is RNA and the matrix with the bound nucleic acid is treated with DNase.

6. The method of claim 1, wherein the nucleic acid is DNA and the matrix with the bound nucleic acid is treated with RNase.

7. The method of claim 1, wherein the sample is a liquid sample selected from plasma, lymph, cerebrospinal fluid, saliva, urine, a tissue extract or a cell culture supernatant.

8. The method of claim 1, wherein the sample is a liquid comprising cells derived from tissue, tissue fragments or cell culture.

9. The method of claim 1, wherein the nucleic acid-retaining separation matrix is selected from a group consisting of magnetic glass particles, silica particles and silica membrane.

10. The method of claim 1, wherein the semipermeable polymer membrane is selected from a group consisting of cellulose acetate, nylon, polyether, and polyether sulfone.

11. The method of isolating viral nucleic acids comprising
    (a) providing a liquid sample;
    (b) obtaining a first precipitate from the sample;
    (c) contacting the first precipitate with a first lysis buffer comprising a reducing agent, a detergent, and a carrier molecule;
    (d) obtaining a second precipitate;
    (e) contacting the second precipitate with a second lysis buffer comprising a protease under the conditions where protease is active;
    (f) obtaining a third precipitate;
    (g) contacting the third precipitate with a buffer comprising an alcohol;
    (h) contacting the sample from step (g) to nucleic acid-retaining separation matrix to bind the nucleic acid;
    (i) contacting the matrix from step (h) with a wash solution;
    (j) eluting the nucleic acid with elution buffer to obtain elution volume;
    (k) pooling at least two elution volumes from the same sample; and
    (l) concentrating the pooled elution volume from step (k) at least 2-fold by passing the pooled elution volume through a semipermeable polymer membrane.

12. The method of claim 11, wherein the sample comprises viral nucleic acid at least 2000 nucleotides long.

13. The method of claim 12, wherein the viral nucleic acid is present at a viral load of less than 10,000 copies per milliliter of sample.

* * * * *